US012805772B2

(12) United States Patent
Van Dinther et al.

(10) Patent No.: US 12,805,772 B2
(45) Date of Patent: Nov. 24, 2026

(54) ARTERIAL BLOOD OXYGENATION MEASUREMENTS

(71) Applicant: KONINKLIJKE PHILIPS N.V., Eindhoven (NL)

(72) Inventors: Cornelus Hendricus Bertus Arnoldus Van Dinther, Mierlo (NL); Laurentia Johanna Huijbregts, Eindhoven (NL); Ercan Ferit Gigi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 471 days.

(21) Appl. No.: 18/272,880

(22) PCT Filed: Jan. 17, 2022

(86) PCT No.: PCT/EP2022/050879
§ 371 (c)(1),
(2) Date: Jul. 18, 2023

(87) PCT Pub. No.: WO2022/157116
PCT Pub. Date: Jul. 28, 2022

(65) Prior Publication Data

US 2023/0404444 A1 Dec. 21, 2023

(30) Foreign Application Priority Data

Jan. 21, 2021 (EP) .................................... 21152719

(51) Int. Cl.
*A61B 5/1455* (2006.01)
*A61B 5/00* (2006.01)
*A61B 5/024* (2006.01)

(52) U.S. Cl.
CPC ...... *A61B 5/14551* (2013.01); *A61B 5/02416* (2013.01); *A61B 5/7239* (2013.01); *A61B 5/7257* (2013.01)

(58) Field of Classification Search
CPC ............ A61B 5/14551; A61B 5/02416; A61B 5/7239; A61B 5/7257; A61B 5/7203; A61B 5/7207
See application file for complete search history.

(56) References Cited

U.S. PATENT DOCUMENTS 6,574,491 B2 6/2003 Elghazzawi
6,631,281 B1 10/2003 Kaestle
(Continued)

FOREIGN PATENT DOCUMENTS

ES 2276594 A1 6/2007

OTHER PUBLICATIONS

International Search Report Dated May 9, 2022 For International Application No. PCT/EP2022/050879 Filed Jan. 17, 2022.
(Continued)

*Primary Examiner* — Abid A Mustansir

(57) ABSTRACT

According to an aspect, there is provided a computer-implemented method for determining an arterial blood oxygenation, SpO2, measurement for a subject. The method comprises receiving (101) a first and second photoplethysmogram, PPG, signals for the subject. The first PPG signal is obtained using a first wavelength of light and the second PPG signal is obtained using a second wavelength of light, and the first and second PPG signals comprise pulse components relating to blood volume changes in the subject over time. The method also comprises determining (103) a fundamental frequency corresponding to a pulse rate of the subject occurring during the measurement of the first and second PPG signals, and processing (105) one or more higher harmonics of the pulse components of the first and second PPG signals at frequencies higher than the fundamental frequency, excluding the fundamental frequency of the pulse components, to determine an SpO2 measurement for the subject.

20 Claims, 6 Drawing Sheets

(56) References Cited

U.S. PATENT DOCUMENTS

| | | | | |
|---|---|---|---|---|
| 7,139,599 | B2 | 11/2006 | Terry | |
| 8,073,516 | B2 | 12/2011 | Scharf | |
| 9,066,660 | B2 | 6/2015 | Watson | |
| 2002/0007114 | A1 | 1/2002 | Elghazzawi | |
| 2011/0077531 | A1* | 3/2011 | Watson ................ | A61B 5/0205 702/19 |
| 2016/0022145 | A1* | 1/2016 | Mostov ................ | A61B 5/7228 340/870.07 |
| 2017/0127981 | A1* | 5/2017 | Vermeulen ........... | A61B 5/0059 |

OTHER PUBLICATIONS

Yousefi Rasoul et al: “A Motion-Tolerant Adaptive Algorithm for Wearable Photoplethysmographic Biosensors”, IEEE Journal of Biomedical and Heal 1H Informatics, IEEE, Piscataway, NJ, USA, vol. 18, No. 2, Mar. 1, 2014 (Mar. 1, 2014), pp. 670-681.

M. van Gastel, S. Stuijk and G. de Haan “New principle for measuring arterial blood oxygenation, enabling motion-robust remote monitoring” (2016), Scientific Reports vol. 6, Article No. 38609).

J.M. Goldman et al. Masimo SET (signal extraction technology) method (“Masimo signal extraction pulse oximetry” (2000), JCMC 16: 475-483).

* cited by examiner

ARTERIAL BLOOD OXYGENATION MEASUREMENTS

CROSS-REFERENCE TO PRIOR APPLICATIONS

This application is the U.S. National Phase application under 35 U.S.C. § 371 of International Application No. PCT/EP2022/050879, filed on Jan. 17, 2022, which claims the benefit of European Application Ser. No. 21/152,719.7 filed on Jan. 21, 2021. These applications are hereby incorporated by reference herein.

FIELD OF THE INVENTION

This disclosure relates to arterial blood oxygenation measurements, and in particular to a computer-implemented method, a computer program product and an apparatus for determining arterial blood oxygenation measurements from photoplethysmogram, PPG, signals.

BACKGROUND OF THE INVENTION

US20020007114A1 relates to detecting a desired physiological parameter from physiological electrical signals, and more particularly to removing artifacts from the physiological signal in order to more accurately detect the desired parameter.

U.S. Pat. No. 7,139,599B2 discloses cepstral domain pulse oximetry.

The article YOUSEFI RASOUL ET AL: "A Motion-Tolerant Adaptive Algorithm for Wearable Photoplethysmographic Biosensors", IEEE JOURNAL OF BIOMEDICAL AND HEALTH INFORMATICS, IEEE, PISCATAWAY, NJ, USA, vol. 18, no. 2, 1 Mar. 2014 (2014-03-01), pages 670-681, also discloses background art.

Pulse oximetry is a widely used non-invasive method to measure a person's arterial blood oxygenation ($SpO_2$). The most commonly used oximeters are placed on the fingertip, toe or earlobe and are often used for patient monitoring in hospitals. When $SpO_2$ needs to be measured under centralisation (i.e. a narrowing of the peripheral vessels), the forehead or nose are preferred locations. Sensors at the above-mentioned locations have disadvantages for the patient, because they may hinder using the hand, may get uncomfortable due to the pressure applied, or the patient may have aesthetical objections. More recently, remote measurement of $SpO_2$ with a camera has been introduced. Camera-based monitoring does not have the above-mentioned disadvantages and may even be used for people with a sensitive skin, for example preterm infants. However, for camera-based monitoring, the subject needs to be in view of the camera.

Sensors or sensor units are being developed that are to be worn on the body to measure various different physiological characteristics of a subject over relatively long periods of time. One suitable location for such sensors or sensor units is the chest. However, pulse oximetry on the chest has challenges: 1) the chest is constantly in motion as a result of respiration, inducing motion artefacts; 2) the composition of tissue and bone may differ depending on the location on the chest; and 3) the measured blood perfusion is low (which could be due to the use of reflective sensors instead of transmissive sensors that are able to be used on peripheral body parts, such as fingertips, toes, earlobe, forehead etc.). Results of a volunteer study revealed a large variance of $SpO_2$ values across subjects (healthy volunteers inhaling normal air) with a chest-worn pulse oximetry sensor, whereas the variance of $SpO_2$ values acquired from a fingertip-worn pulse oximetry sensor was much smaller.

SUMMARY OF THE INVENTION

There is therefore a need for improvements in the measurement of arterial blood oxygenation ($SpO_2$) of a subject. The invention is defined by the independent claims. The dependent claims define advantageous embodiments.

The techniques described herein provide solutions for pulse oximetry at locations on the body of a subject where the measured pulsatile component (i.e. the measured blood flow) is disturbed by physical noise or motion artefacts, such as respiration (breathing) Such locations can include the chest, for example at the $2^{nd}$ intercostal on the mid-clavicle line, at the left side of the upper chest. At such positions $SpO_2$ measurement is unreliable using conventional algorithmic methods.

Conventional pulse oximetry determines $SpO_2$ based on the method of "ratio-of-ratios". The optical density ratio can be derived from PPG signals at two different wavelengths (e.g. red and infrared) in the time-domain or spectral-domain. The PPG signals include signal components due to the pulse/blood volume changes (these are referred to herein as the 'pulse components' of the PPG signal), and signal components due to noise and/or motion artefacts (including motion due to respiration). The pulse components of the PPG signal are a harmonic series in the PPG signal, with the pulse rate as the fundamental frequency (first harmonic) of the harmonic series. Thus, the pulse components include signal components at the pulse rate, and signal components at higher harmonics, i.e. at frequencies above the pulse rate. The techniques described herein are based on the insight that $SpO_2$ can be determined from the higher harmonics of the pulse components in the multi-colour (different wavelength) PPG signals. Conventional spectral-domain methods for determining $SpO_2$ always take the fundamental frequency (the first harmonic) of the pulse components of the PPG signals into consideration. Excluding the fundamental frequency of the pulse components from consideration provides improvements in the reliability of $SpO_2$ measurements.

According to a first specific aspect, there is provided a computer-implemented method for determining a $SpO_2$ measurement for a subject. The method comprises: receiving a first and second PPG signals for the subject, wherein the first PPG signal is obtained using a first wavelength of light and the second PPG signal is obtained using a second wavelength of light, wherein the first and second PPG signals comprise pulse components relating to blood volume changes in the subject over time; determining a fundamental frequency corresponding to a pulse rate of the subject occurring during the measurement of the first and second PPG signals; and processing one or more higher harmonics of the pulse components of the first and second PPG signals at frequencies higher than the fundamental frequency to determine an $SpO_2$ measurement for the subject based on the processed one or more higher harmonics of the pulse components of the first and second PPG signals, excluding the fundamental frequency of the pulse components. Thus, the fundamental frequency of the pulse components is excluded from consideration when determining $SpO_2$ measurements, which improves the reliability of $SpO_2$ measurements.

In some embodiments, the step of processing comprises processing the one or more higher harmonics of the pulse components of the first and second PPG signals in the time domain or frequency domain to determine the $SpO_2$ measurement. Thus, the first aspect is not limited to determining $SpO_2$ by processing the PPG signals in a specific domain.

In some embodiments, the step of processing comprises: applying respective weightings to the one or more higher harmonics; and processing the weighted higher harmonics to determine the $SpO_2$ measurement. These embodiments recognise that certain higher harmonics may be more useful for determining reliable $SpO_2$ measurements, and therefore the weightings can increase the contribution of that/those higher harmonic(s) to the $SpO_2$ measurement. In these embodiments, the respective weightings may be based on one or more of a respiration rate of the subject, a pulse rate of the subject, a position of a PPG sensor on the subject or relative to the subject, and measurements of movement and/or posture of the subject.

In alternative embodiments, the step of processing comprises: selecting one or more higher harmonics of the pulse components of the first and second PPG signals; and processing the selected one or more higher harmonics to determine the $SpO_2$ measurement. These embodiments recognise that certain higher harmonics may be more useful for determining reliable $SpO_2$ measurements than others, and therefore only that/those higher harmonic(s) are used to determine the $SpO_2$ measurement. In these embodiments, the step of selecting the one or more higher harmonics may comprise selecting one or more higher harmonics based on one or more of a respiration rate of the subject, a pulse rate of the subject, a position of a PPG sensor on the subject or relative to the subject, and measurements of movement and/or posture of the subject.

In alternative embodiments, the step of processing comprises: high-pass filtering the first and second PPG signals with a cut-off frequency above the fundamental frequency; and processing the high-pass filtered first and second PPG signals to determine the $SpO_2$ measurement. In these embodiments, the high-pass filtered first and second PPG signals may be processed in the time domain to determine the $SpO_2$ measurement. In these embodiments, the cut-off frequency may be selected based on one or more of a respiration rate of the subject, a pulse rate of the subject, a position of a PPG sensor on the subject or relative to the subject, and measurements of movement and/or posture of the subject.

In some embodiments, the step of processing one or more higher harmonics comprises: determining the $SpO_2$ measurement from an optical density ratio derived from the one or more higher harmonics of the first and second PPG signals. Thus, these embodiments apply the use of higher harmonics to the ratio-of-ratios approach to determining $SpO_2$.

In alternative embodiments, the step of processing one or more higher harmonics comprises: determining the $SpO_2$ measurement from amplitudes of the one or more higher harmonics.

In some embodiments, the step of determining the fundamental frequency comprises processing the first and/or second PPG signals to determine the fundamental frequency. These embodiments provide the advantage that a separate sensor is not required for measuring the pulse rate or heart rate.

According to a second aspect, there is provided a computer program product comprising a computer readable medium having computer readable code embodied therein, the computer readable code being configured such that, on execution by a suitable computer or processor, the computer or processor is caused to perform the method according to the first aspect or any embodiment thereof.

According to a third aspect, there is provided an apparatus for determining a $SpO_2$ measurement for a subject. The apparatus comprises a processing unit configured to: receive first and second PPG signals for the subject, wherein the first PPG signal is obtained using a first set of wavelengths of light and the second PPG signal is obtained using a second set of wavelengths of light, wherein the first and second PPG signals comprise pulse components relating to blood volume changes in the subject over time; determine a fundamental frequency corresponding to a pulse rate of the subject occurring during the measurement of the first and second PPG signals; and process one or more higher harmonics of the pulse components of the first and second PPG signals at frequencies higher than the fundamental frequency to determine an $SpO_2$ measurement for the subject based on the processed one or more higher harmonics of the pulse components of the first and second PPG signals, excluding the fundamental frequency of the pulse components. Thus, the fundamental frequency of the pulse components is excluded from consideration when determining $SpO_2$ measurements, which improves the reliability of $SpO_2$ measurements.

In some embodiments, the processing unit is configured to process the one or more higher harmonics of the pulse components of the first and second PPG signals in the time domain or frequency domain to determine the $SpO_2$ measurement. Thus, the third aspect is not limited to determining $SpO_2$ by processing the PPG signals in a specific domain.

In some embodiments, the processing unit is configured to process the one or more higher harmonics of the pulse components by: applying respective weightings to the one or more higher harmonics; and processing the weighted higher harmonics to determine the $SpO_2$ measurement. These embodiments recognise that certain higher harmonics may be more useful for determining reliable $SpO_2$ measurements, and therefore the weightings can increase the contribution of that/those higher harmonic(s) to the $SpO_2$ measurement. In these embodiments, the respective weightings may be based on one or more of a respiration rate of the subject, a pulse rate of the subject, a position of a PPG sensor on the subject or relative to the subject, and measurements of movement and/or posture of the subject.

In alternative embodiments, the processing unit is configured to process the one or more higher harmonics of the pulse components by: selecting one or more higher harmonics of the pulse components of the first and second PPG signals; and processing the selected one or more higher harmonics to determine the $SpO_2$ measurement. These embodiments recognise that certain higher harmonics may be more useful for determining reliable $SpO_2$ measurements than others, and therefore only that/those higher harmonic(s) are used to determine the $SpO_2$ measurement. In these embodiments, the processing unit can be configured to select the one or more higher harmonics based on one or more of a respiration rate of the subject, a pulse rate of the subject, a position of a PPG sensor on the subject or relative to the subject, and measurements of movement and/or posture of the subject.

In alternative embodiments, the processing unit is configured to process the one or more higher harmonics of the pulse components by: high-pass filtering the first and second PPG signals with a cut-off frequency above the fundamental frequency; and processing the high-pass filtered first and second PPG signals to determine the $SpO_2$ measurement. In these embodiments, the high-pass filtered first and second PPG signals may be processed in the time domain to determine the $SpO_2$ measurement. In these embodiments, the cut-off frequency may be selected based on one or more of a respiration rate of the subject, a pulse rate of the subject, a position of a PPG sensor on the subject or relative to the subject, and measurements of movement and/or posture of the subject.

In some embodiments, the processing unit is configured to process the one or more higher harmonics of the pulse components by: determining the $SpO_2$ measurement from an optical density ratio derived from the one or more higher harmonics of the first and second PPG signals. Thus, these embodiments apply the use of higher harmonics to the ratio-of-ratios approach to determining $SpO_2$.

In alternative embodiments, the processing unit is configured to determine the $SpO_2$ measurement from amplitudes of the one or more higher harmonics.

In some embodiments, the processing unit is configured to determine the fundamental frequency by processing the first and/or second PPG signals to determine the fundamental frequency. These embodiments provide the advantage that a separate sensor is not required for measuring the pulse rate or heart rate.

In alternative embodiments, the processing unit is further configured to receive a measurement signal from a pulse rate sensor, and to determine the pulse rate by processing the measurement signal. In some embodiments, the apparatus further comprises the pulse rate sensor. In alternative embodiments, the processing unit is configured to receive the measurement signal from a pulse rate sensor separate from the apparatus.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
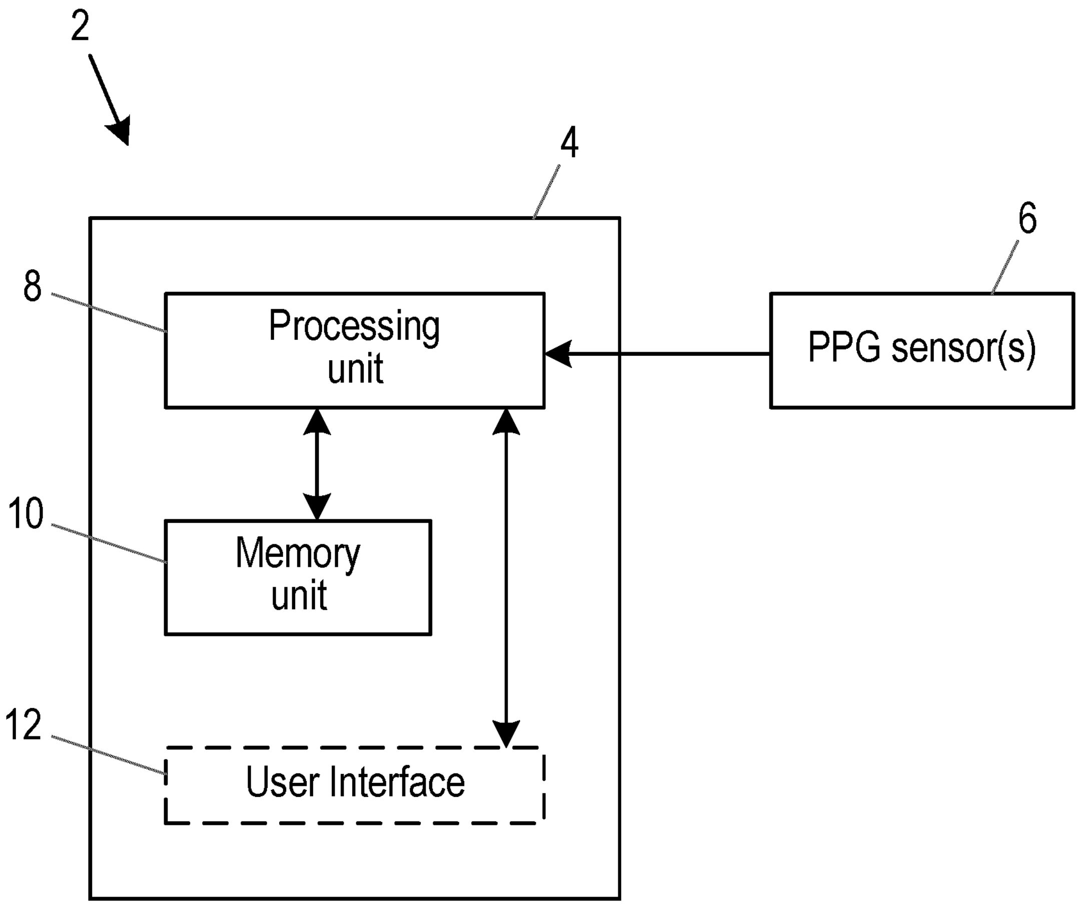
FIG. 1 is a block diagram of an apparatus that can be used to implement the techniques described herein.

FIG. 1 is a block diagram of a system 2 according to various embodiments for determining an $SpO_2$ measurement for a subject. The system 2 comprises an apparatus 4 that operates according to the techniques described herein to determine $SpO_2$ measurements from PPG signals obtained using one or more PPG sensors 6. The system 2 can be referred to as a pulse oximetry system or a pulse oximeter.

The PPG sensor(s) 6 are to be placed on the body of the subject and output PPG signals that are related to the volume of blood passing through that part of the body. For an $SpO_2$ measurement, PPG signals are required for at least two different wavelengths of light, typically one wavelength in the red part of the spectrum and one wavelength in the infrared part of the spectrum, although in some embodiments a third PPG signal for a different wavelength of light can also be used. In some embodiments, a single PPG sensor 6 can be used that is capable of obtaining respective PPG signals for different wavelengths of light. In other embodiments, multiple PPG sensors 6 are used that each obtain a respective PPG signal for one particular wavelength of light.

As known to those skilled in the art, a PPG sensor 6 comprises a light sensor, and typically one or more light sources. The light sensor can be positioned with respect to the light source(s) so that the light sensor measures the light passing through the body part from the one or more light sources (a so-called transmissive arrangement), or the light sensor can be positioned with respect to the light source(s) so that the light sensor measures the light from the light source(s) that is reflected from the body part (a so-called reflective arrangement). In the case of a chest-worn PPG sensor 6, the PPG sensor 6 may use a reflective arrangement, whereas for a peripheral body location, such as a fingertip, a transmissive arrangement can be used.

The PPG signal(s) output by the PPG sensor(s) 6 are typically a raw measurement signal from the light sensor for a particular wavelength of light. For example, the PPG signal can be a signal or time series of measurement samples representing light intensity of light at a particular wavelength over time.

Although the one or more PPG sensors 6 are shown in FIG. 1 as being separate from the apparatus 4, in alternative embodiments the one or more PPG sensor(s) 6 may be part of the apparatus 4.

The apparatus 4 may be in the form of, or be part of, a computing device, such as a server, desktop computer, laptop, tablet computer, smartphone, smartwatch, sensor patch, etc. The apparatus 4 includes a processing unit 8 that controls the operation of the apparatus 4 and that can be configured to execute or perform the methods described herein. In particular the processing unit 8 receives the PPG signals from the PPG sensor(s) 6.

The processing unit 8 can be implemented in numerous ways, with software and/or hardware, to perform the various functions described herein. The processing unit 8 may comprise one or more microprocessors or digital signal processors (DSPs) that may be programmed using software or computer program code to perform the required functions and/or to control components of the processing unit 8 to effect the required functions. The processing unit 8 may be implemented as a combination of dedicated hardware to perform some functions (e.g. amplifiers, pre-amplifiers, analog-to-digital convertors (ADCs) and/or digital-to-analog convertors (DACs)) and a processor (e.g., one or more programmed microprocessors, controllers, DSPs and associated circuitry) to perform other functions. Examples of components that may be employed in various embodiments of the present disclosure include, but are not limited to, conventional microprocessors, DSPs, application specific integrated circuits (ASICs), field-programmable gate arrays (FPGAs), hardware for implementing a neural network and/or so-called artificial intelligence (AI) hardware accelerators (i.e. a processor(s) or other hardware specifically designed for AI applications that can be used alongside a main processor).

The processing unit 8 is connected to a memory unit 10 that can store data, information and/or signals for use by the processing unit 8 in controlling the operation of the apparatus 4 and/or in executing or performing the methods described herein. In some implementations the memory unit 10 stores computer-readable code that can be executed by the processing unit 8 so that the processing unit 8 performs one or more functions, including the methods described herein. In particular embodiments, the program code can be in the form of an application for a smartwatch, smartphone, tablet, laptop or computer. The memory unit 10 can comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM) and electrically erasable PROM (EEPROM), and the memory unit 10 can be implemented in the form of a memory chip, an optical disk (such as a compact disc (CD), a digital versatile disc (DVD) or a Blu-Ray disc), a hard disk, a tape storage solution, or a solid state device, including a memory stick, a solid state drive (SSD), a memory card, etc.

In some embodiments, the apparatus 4 comprises a user interface 12 that includes one or more components that enables a user of apparatus 4 to input information, data and/or commands into the apparatus 4, and/or enables the apparatus 4 to output information or data to the user of the apparatus 4. Information that can be output by the user interface 12 can include an $SpO_2$ measurement. The user interface 12 can comprise any suitable input component(s), including but not limited to a keyboard, keypad, one or more buttons, switches or dials, a mouse, a track pad, a touchscreen, a stylus, a camera, a microphone, etc., and/or the user interface 12 can comprise any suitable output component(s), including but not limited to a display screen, one or more lights or light elements, one or more loudspeakers, a vibrating element, etc.

It will be appreciated that a practical implementation of an apparatus 4 may include additional components to those shown in FIG. 1. For example the apparatus 4 may also include a power supply, such as a battery, or components for enabling the apparatus 4 to be connected to a mains power supply. The apparatus 4 may also include interface circuitry for enabling a data connection to and/or data exchange with other devices or sensors. For example, in embodiments where the PPG sensor(s) 6 are separate from the apparatus 4, the PPG signals can be received from the PPG sensor(s) 6 via the interface circuitry. Furthermore, in some embodiments the system 2 can be for measuring additional physiological characteristics of the subject, in which case the system 2 can comprise one or more additional sensors that are used to measure these physiological characteristics of the subject.

As mentioned above, conventional pulse oximetry determines $SpO_2$ based on the so-called method of "ratio-of-ratios". The optical density ratio r is determined by the ratio of the pulsatile (pulse) components in the red light PPG signal ($AC_{RD}$) normalised by its non-pulsatile (non-pulse) components ($DC_{RD}$) and the pulsatile (pulse) components in the infrared light PPG signal ($AC_{IR}$) normalised by its non-pulsatile (non-pulse) components ($DC_{IR}$), i.e.

$$r = \frac{AC_{RD} / DC_{RD}}{AC_{IR} / DC_{IR}} \quad (1)$$

The pulsatile/pulse components in the PPG signal are caused by the changes in blood volume in the subject due to heart beats. As noted above, the pulsatile/pulse components are a harmonic series with the pulse rate as the fundamental frequency/first harmonic, and thus the pulsatile/pulse components include signal components at a frequency corresponding to the pulse rate and signal components at frequencies higher than the pulse rate, including higher harmonics of the pulse components. The optical density ratio r can be mapped to $SpO_2$ values using an empirical calibration step, e.g. $SpO_2=110-25 \cdot r$.

An example of a spectral-domain based method for deriving the optical density ratio r is FAST, as described in U.S. Pat. No. 6,631,281. The FAST method determines the ratio based on the individual spectra of normalised red and normalised infrared signals. A representation of needle-like tips are obtained by plotting the infrared spectrum in the ordinate direction and the red spectrum in the abscissa direction. The needles correspond to the peaks in the infrared and red spectra and the direction of the needles corresponds to the saturation. Conventionally, the $SpO_2$ is mainly determined by the fundamental frequency of the pulse signal, since the fundamental frequency of the pulse signal is dominant in the amplitude spectrum compared to its higher harmonics.

As noted above, the techniques described herein are based on the insight that $SpO_2$ can be determined from the higher harmonics of the pulse component(s) in the different wavelength PPG signals. Excluding the fundamental frequency (first harmonic) of the pulse components of the PPG signals from consideration provides improvements in the reliability of $SpO_2$ measurements. Thus, according to the techniques described herein, an $SpO_2$ measurement is determined by processing the parts of the pulse components of the PPG signals that have frequencies higher than the fundamental frequency (first harmonic) of the pulse components. In some embodiments, an $SpO_2$ measurement is determined by processing one or more of the higher harmonics of the pulse components of the PPG signals. The fundamental frequency is the pulse rate of the subject during the measurement of the PPG signals. In the following, 'higher harmonics' refers to harmonics of the pulse component of the waveform above the pulse rate (where the pulse rate is the first harmonic/fundamental frequency).

A method based on noise cancellation (NC) related to the adaptive pulse blood volume (APBV) method (e.g. as described in "New principle for measuring arterial blood oxygenation, enabling motion-robust remote monitoring" by M. van Gastel, S. Stuijk and G. de Haan (2016), Scientific Reports volume 6, Article number: 38609) and the Masimo SET (signal extraction technology) method ("*Masimo signal extraction pulse oximetry*" by J. M. Goldman et al. (2000), *JCMC* 16: 475-483) is used below to demonstrate the improvements obtained by using only the higher harmonics of the pulse component according to the techniques described herein. The NC method is similar to the APBV and Masimo SET method in that it inverts the process of measuring $SpO_2$. It examines a collection of ratios and determines $SpO_2$ from the ratio which produces the highest pulse quality signal extracted from the PPG waveforms. The pulse quality is determined by the periodicity of the pulse signal, i.e. the power spectrum of the pulse signal is normalised by a scaling factor such that a completely periodic signal will have a summed peak level (summation of harmonically related peaks) equal to unity, while any non-harmonic or non-periodic distortion will decrease this peak level.

In embodiments of the techniques described herein, the candidate pulse signals (i.e. the PPG signals obtained using different wavelengths of light) can be analysed for the amount of periodicity determined from the higher harmonics, e.g. harmonics above a certain frequency, say 2.5 Hz, or determined from a certain harmonic number.

Improvements in the $SpO_2$ measurements provided by the techniques presented herein are shown based on results from a study conducted on five healthy volunteers. In this study, respective red and infrared PPG signals were obtained for three different locations on the body simultaneously. These locations were the fingertip, the sternum and on the chest, and specifically at the $2^{nd}$ intercostal on the mid-clavicle line, at the left side of the upper chest.

Figure 2:
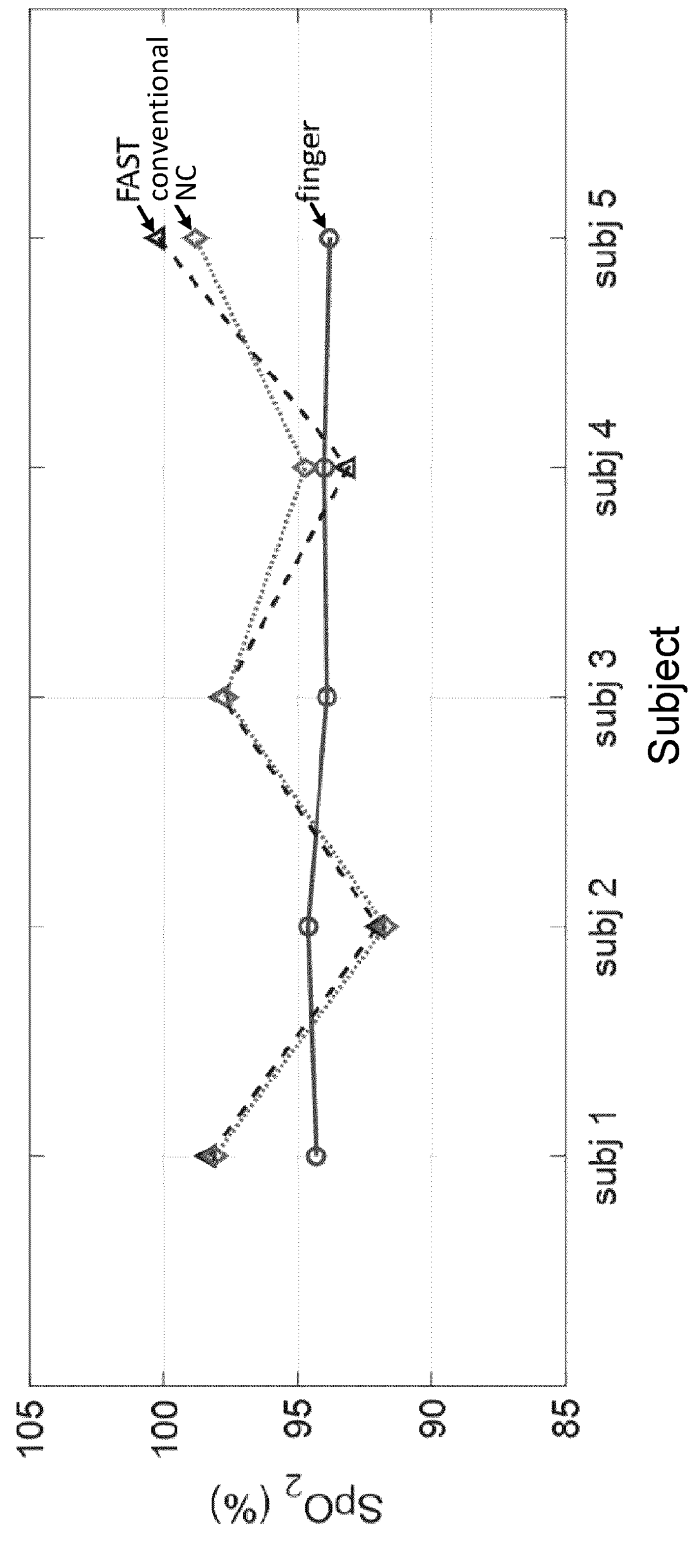
FIG. 2 is a graph illustrating $SpO_2$ measurements obtained according to conventional techniques for five subjects obtained at the chest and fingertip locations.

Firstly, the graph in FIG. 2 shows averaged $SpO_2$ measurements over a 2-minute period computed by two conventional methods (FAST and NC) for PPG sensors positioned on the chest, and conventional $SpO_2$ measurements on the fingertip that are averaged values obtained from the two methods, since the values were almost identical across methods. It should be noted that the comparison across methods is focused on the spread in $SpO_2$ values and not on the absolute values, since in the study the $SpO_2$ sensor positioned on the chest was not calibrated. The NC method shown in FIG. 2 is not making use of the techniques described herein, i.e. the NC method makes use of the fundamental frequency to compute $SpO_2$.

Thus, it can be seen in FIG. 2 that for most of the subjects there are significant differences between the $SpO_2$ obtained at the fingertip, and the $SpO_2$ obtained using the FAST and NC techniques. FIG. 2 shows that measurements obtained from the fingertip lie around 94%, with a small variance across subjects. Measurements obtained on the chest clearly vary much more across subjects, with values ranging between 92% and 100%. The variance of $SpO_2$ when measured on the chest is far too large compared with the variance of $SpO_2$ measured at the fingertip, and a comparison with a reference would certainly exceed the root-mean-square error (RMSE) limit of 3.5%, the requested limit of the US Food and Drug Administration (FDA).

Figure 3:
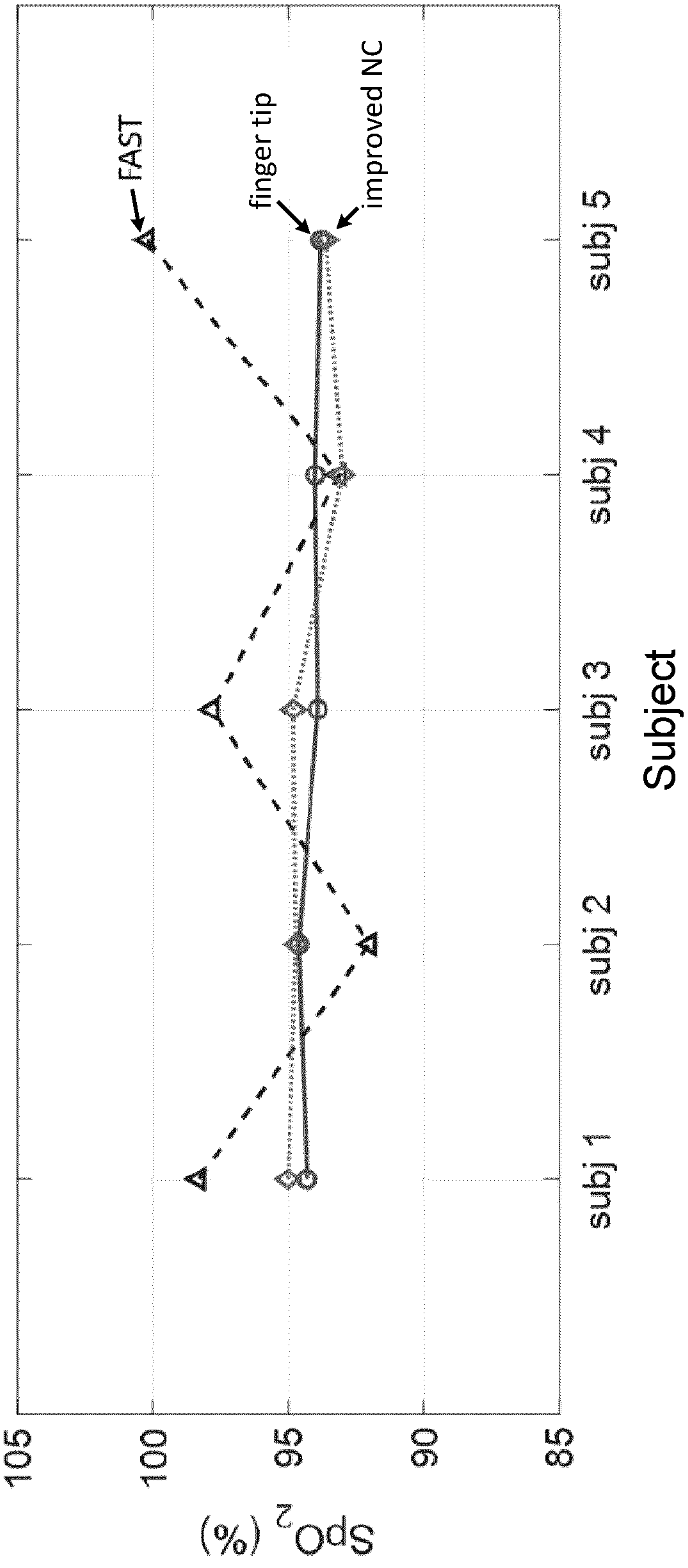
FIG. 3 is a graph illustrating $SpO_2$ measurements obtained according to embodiments of the techniques described herein for five subjects obtained at the chest and fingertip locations.

The graph in FIG. 3 shows the same averaged $SpO_2$ measurements as in FIG. 2, except that the NC technique used to determine $SpO_2$ only makes use of the higher harmonics to determine $SpO_2$ and not the fundamental frequency of the pulse. It can be seen in FIG. 3 that the variance of the $SpO_2$ measurements determined at the chest using the improved NC method is significantly reduced compared to the FAST method and the conventional NC method, and is now much closer to the variance of $SpO_2$ measured at the fingertip.

It is considered that the improvements provided by only using the higher harmonics to determine the $SpO_2$ measurement could be due to motion artefacts stemming from respiration mainly affecting the lower frequency range, since respiration rate is usually lower than pulse rate, and having less impact on the higher harmonics of the pulse components. It may also be the case that the venous blood pulse mainly affects the lower frequency range, and its higher harmonics are less present compared with the higher harmonics of the arterial blood pulse.

While in some embodiments all harmonics above the fundamental frequency are used to determine the $SpO_2$ measurement, in alternative embodiments a selection of one or more higher harmonics may be made, and the $SpO_2$ measurement determined from an analysis of those harmonic(s) in the PPG signals. In the latter case, the selection of the one or more higher harmonics may be dynamic and depend on one or more parameters. The parameters could include vital signs such as heart rate (pulse rate) or respiration rate, or parameters related to the stiffness of blood vessels, such as the age of the subject, pulse transit time (PTT), and/or the morphology of the pulse wave.

Thus, in some embodiments if respiration rate increases or is above a threshold value, then the $SpO_2$ measurement may be determined from a higher frequency region or at higher harmonic numbers of the pulse spectrum, rather than all of the higher harmonics of the pulse component in the PPG signals. For example, a respiration rate of 25 breaths per minute may be above a respiration rate threshold, and so at this respiration rate the $SpO_2$ measurement may be determined from frequencies above the second harmonic of the pulse component. If in this example the pulse rate is at 60 beats per minute, the $SpO_2$ measurement can be determined using the third and higher harmonics at 180 beats per minute.

In some embodiments, if the pulse rate increases or is above a threshold value, then the $SpO_2$ measurement may be determined from an even higher frequency region or at harmonic numbers of the pulse spectrum above the second harmonic, rather than just the second harmonic components and higher of the pulse component in the PPG signals. For example, a pulse rate of 120 beats per minute (bpm) may be above a pulse rate threshold, and so the $SpO_2$ measurement may be determined from frequencies above the second harmonic of the pulse component (e.g. the third harmonic and higher).

In some embodiments, the higher harmonic(s) to use to determine $SpO_2$ may be determined based on both the respiration rate and the pulse rate of the subject. For example, consideration can be given to the harmonics of the respiration components in the PPG signal in determining which higher harmonics of the pulse components should be used to determine $SpO_2$. For example, if the pulse rate is relatively low, the $SpO_2$ measurement may be determined from third or higher harmonics of the pulse components where the second harmonic of the respiration components is close to the pulse rate. For example, if the pulse rate is 55 bpm and the respiration rate is 25 breaths per minute, the second harmonic of the respiration components is close to the pulse rate. The third harmonic of the pulse components (i.e. 165 bpm) may be less distorted by the sixth and seventh harmonics of the respiration components (i.e. 150 breaths per minute and 175 breaths per minute respectively), and amplitudes of harmonics usually decrease for increasing harmonic number.

To implement the above embodiments, the apparatus 4 or system 2 may further comprise one or more other sensors for measuring a vital sign such as the pulse rate and/or respiration rate (with such sensor(s) being referred to as a 'pulse rate sensor' and a 'respiration rate sensor' respectively. For example, the apparatus 4 or system 2 may comprise an electrocardiogram (ECG) sensor, a ballistocardiogram (BCG) sensor, a resistive sensor, a capacitive sensor, an inductive sensor, a bioimpedance sensor, an air flow sensor, or an accelerometer that can provide a measurement signal representative of a vital sign such as pulse rate and/or respiration rate. These sensor(s) may be worn on the subject, for example at the same or similar location on the body to the PPG sensor(s) 6, or they may be in the environment of the subject, for example in a bed. Alternatively, the pulse rate and/or respiration rate can be determined from one or both of the PPG signals obtained by the PPG sensor(s) 6 that are used to determine the $SpO_2$ measurement. The use of a PPG signal to determine pulse rate is well known in the art.

Furthermore, a respiration rate can be determined by low pass filtering a PPG signal, particularly for a PPG signal obtained from a PPG sensor 6 located on the chest.

In some embodiments, the best harmonics to use to determine $SpO_2$ may depend on the position of the PPG sensors 6 on the body of the subject. For example, based on the study data shown in FIGS. 2 and 3, $SpO_2$ measurements obtained from PPG signals measured at the sternum and fingertips show less difference than PPG signals measured at the chest, for example due to measurements at the chest being influenced by the movement of the chest due to breathing.

Figure 4:
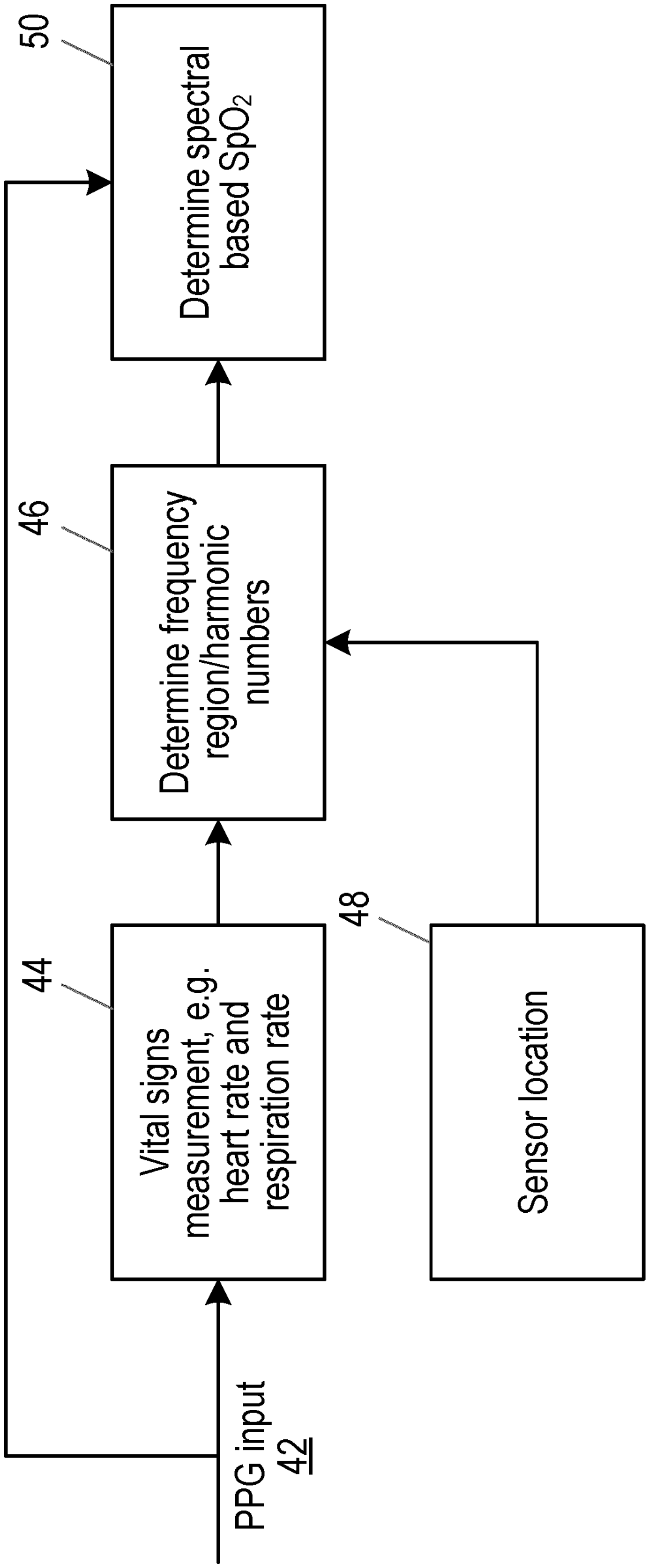
FIG. 4 is a block diagram showing an exemplary process of determining $SpO_2$ measurements according to an embodiment.

FIG. 4 is a block diagram showing an exemplary process of determining $SpO_2$ measurements according to an embodiment. In this embodiment, the selection of the higher harmonics to use to determine $SpO_2$ is based on one or more vital signs, such as pulse rate and/or respiration rate, and also on the position of the PPG sensors on the subject. Thus, PPG signals 42 from PPG sensor(s) 6 are input to a vital signs measurement block 44 that determines a measurement of one or more vital signs or other parameters used to select higher harmonics.

The determined vital signs or other parameters are input to block 46, along with information 48 on the location of the PPG sensor(s) 6. Block 46 then selects a suitable frequency region(s), higher harmonics for determining $SpO_2$ based on the received vital signs or other parameters and the location of the PPG sensor(s) 6.

Information indicating the selected frequency region(s), higher harmonics is output to block 50 that determines the $SpO_2$ measurement using the PPG signals 42 according to the selected frequency region(s), or higher harmonics. In some embodiments, block 50 'tracks' the higher harmonic components by detecting the peaks in the amplitude spectrum. For a standard method of determining $SpO_2$, e.g. using the ratio of ratios, peaks can be detected and tracked in the red and infrared PPG signals 42, and these peaks used to compute $SpO_2$. For alternative methods that are based on NC or APBV, higher harmonic peaks in the amplitude spectrum of the PPG signals can be tracked to find the optimal ratio.

In an alternative approach, some embodiments provide that $SpO_2$ can be measured directly from higher harmonic amplitudes using a method that tracks the higher harmonic frequencies and sums the complex frequency values for each higher harmonic. In this approach, higher harmonics can be tracked by finding or determining the fundamental frequency, and taking an integer multitude of that frequency to get to the higher harmonics. This can be repeated often, for example every 1 second, and the frequency path of these harmonics can be followed.

There are several ways to detect the fundamental frequency. For example, the infrared PPG signal can be analysed to find the first significant peak in the magnitude spectrum of a time window of the infrared PPG signal that has at least two periods of the pulse rate. If the lowest possible pulse rate is 30 bpm, a 4-second window can be sufficient. After applying a proper window function (e.g. a Hanning window), the Fourier Transform can be calculated, and the corresponding magnitude spectrum. All the peaks within the possible frequency range of the pulse rate can be found (for example if the pulse rate can be between 30 and 180 bpm, then peaks between 0.5 Hz and 3 Hz should be searched for). The maximum within this window can be determined, and the first peak that is at least a certain percentage of this maximum (e.g. 20%) can be identified. This first peak is the fundamental frequency.

In the following example, the first significant peak is found at 0.66 Hz (40 bpm). If only frequencies between 150 and 300 bpm are used for an $SpO_2$ measurement, then the magnitudes of the higher harmonics of the fundamental frequency that are between 150 and 300 bpm can be summed. For a fundamental frequency at 40 bpm, the harmonics 4, 5, 6 and 7 fall within this range. Therefore, the magnitude values at these harmonics of the infrared magnitude spectrum are summed. The same can be done for the red PPG signal. The same time windows are used, and the magnitude spectrum calculated. The fundamental frequency is known to be 40 bpm. Therefore the magnitude values are summed at the same harmonics as for the infrared PPG signal. Now that the average magnitude of infrared and red PPG signals are known, the corresponding $SpO_2$ can be calculated using the ratio as described above.

Figure 5:
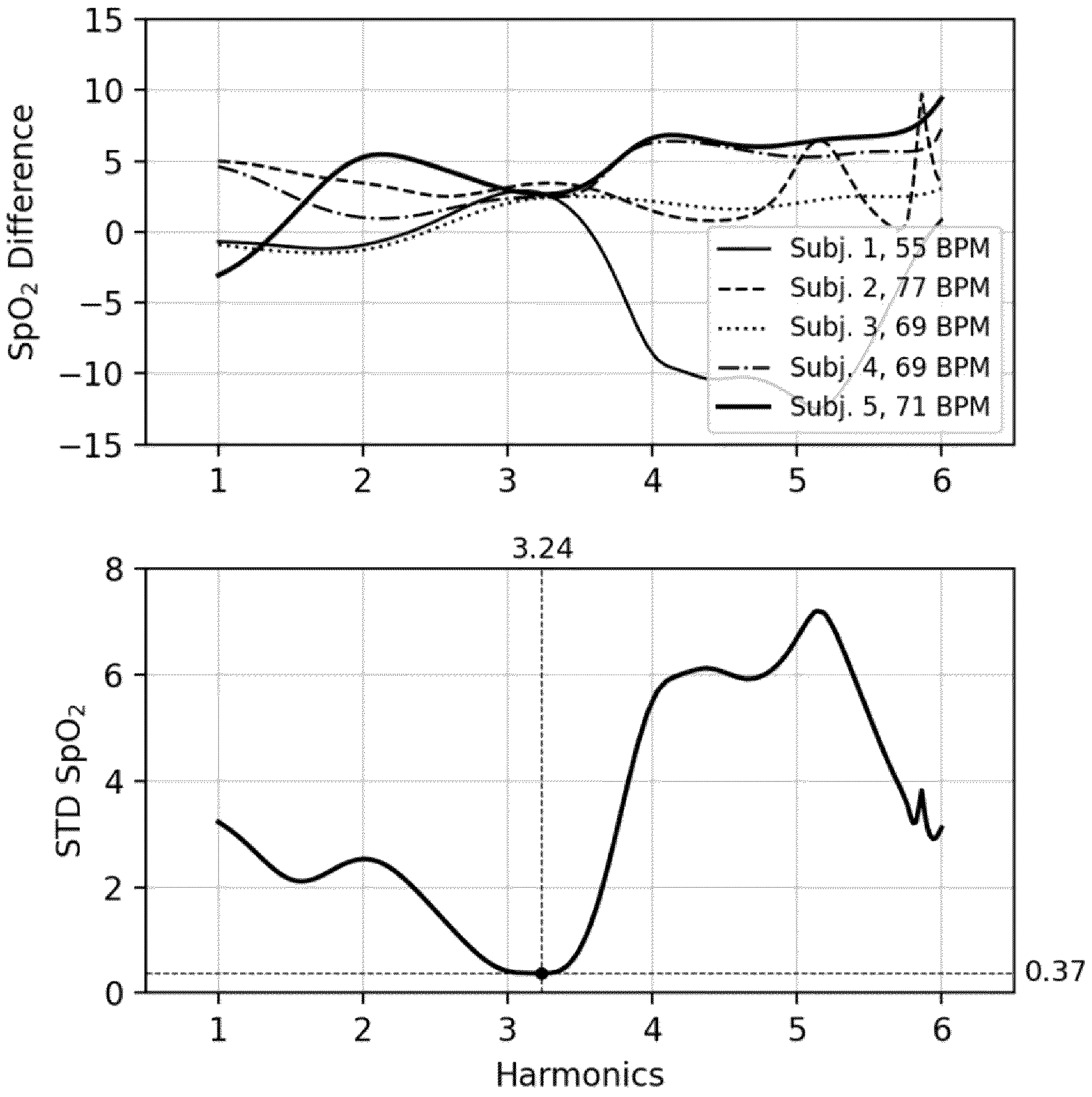
FIG. 5 is two graphs showing the results of an alternative approach for determining $SpO_2$ measurements according to embodiments of the techniques described herein.

FIG. 5 shows the difference of $SpO_2$ values measured using the above approaches against the $SpO_2$ obtained at the fingertip according to conventional methods (the fingertip-based measurement is used as a reference). The top graph in FIG. 5 plots the $SpO_2$ difference for each of five subjects against frequency, with the $1^{st}$-$6^{th}$ harmonic frequencies of the pulse rate labelled on the abscissa. The $SpO_2$ difference represents the difference between the $SpO_2$ measured using the pulse components at that particular frequency and the $SpO_2$ measured at the fingertip using the conventional method. Thus, the line for each subject shows how the $SpO_2$ difference with the conventional fingertip-based measurement changes with frequencies above the fundamental frequency (first harmonic). Usually, $SpO_2$ is measured using the ratio of amplitude values of red and infrared PPG signals at the fundamental frequency (i.e. at harmonic 1), although according to the techniques described herein pulse components at frequencies higher than the fundamental frequency can instead be used to get an $SpO_2$ value, as shown in FIG. 5.

The bottom graph in FIG. 5 plots the standard deviation or spread (denoted STD $SpO_2$) of the $SpO_2$ differences across the subjects at each of the frequencies. The best higher harmonic for determining $SpO_2$ is where the difference with the fingertip-based measurement is lowest over the five subjects. It can be seen that the lowest spread of 0.37% is at harmonic 3.24 (i.e. the frequency that is 3.24*pulse rate). Thus, to the nearest whole harmonic number, the difference with the fingertip-based measurement is lowest at the $3^{rd}$ harmonic, and in some embodiments the $SpO_2$ measurement based on a ratio of ratios calculated from the pulse components at the $3^{rd}$ harmonic, or the pulse components at the $3.24^{th}$ harmonic. It will be appreciated that the $SpO_2$ measurements may not be calibrated, and so there may be an offset that needs to be subtracted from the $SpO_2$ measurements. As a result, the absolute deviation from the reference fingertip sensor may be less important than the deviation amongst different subjects.

In some embodiments, the analysis of the higher harmonics to determine $SpO_2$ may include applying a weighting to one or more of the harmonics of the pulse components. The weighting for a particular harmonic may reflect the reliability of an $SpO_2$ measurement obtained using that harmonic. For example, referring to the example in the bottom graph of FIG. 5, a higher weighting can be used for the third harmonic and nearby frequencies since $SpO_2$ measurements at these frequencies are closer to a fingertip-based measurement, but lower weightings can be used for the second harmonic and/or the fourth harmonic and higher. In some embodiments, the weighting applied to particular harmonics may also or alternatively depend on one or more vital signs or other parameters of the subject. For example, in a similar way to the selection of suitable higher harmonics, the weighting applied may depend on the pulse rate, the respiration rate and/or the location of the PPG sensor(s) 6 on the body of the subject. This approach can be used in the NC or ABPV method in which a weighted average of the harmonic amplitudes can be used to determine the optimal ratio for determining $SpO_2$.

In addition or alternatively, in some embodiments respective $SpO_2$ measurements are determined from different higher harmonics, and these $SpO_2$ measurements are averaged to determine the final $SpO_2$ measurement. This average may be a weighted average, in which case determining the $SpO_2$ measurement can comprise applying respective weightings to $SpO_2$ measurements determined using respective higher harmonics, and determining the final $SpO_2$ measurement as a weighted average of the weighted $SpO_2$ measurements. The weighting for a particular $SpO_2$ measurement may reflect the reliability of an $SpO_2$ measurement obtained using the relevant harmonic. As above, the weighting for particular $SpO_2$ measurements may also or alternatively depend on one or more vital signs or other parameters of the subject. For example, the weighting applied may depend on the pulse rate, the respiration rate and/or the location of the PPG sensor(s) 6 on the body of the subject. This approach can be used with the standard 'ratio of ratios' method of determining an $SpO_2$ measurement, so, for example, a weighted average can be taken of the $SpO_2$ values computed for each harmonic.

In another approach, the analysis of the higher harmonics may only take into account higher harmonics above a certain frequency. This can be performed in a similar way to the weighting of one or more of the higher harmonics above or forming the weighted average, except that all higher harmonics above the certain frequency are considered when determining the $SpO_2$ measurement.

In other embodiments, the analysis of the higher harmonics may comprise tracking a single higher harmonic, for example the $3^{rd}$ harmonic.

While in the above embodiments the PPG signals are analysed in the spectral (frequency) domain, in some embodiments the evaluation of the higher harmonics of the pulse components can be applied to analysis of the PPG signals in the time domain. In particular, the PPG signals can be high-pass filtered with a cut-off frequency above the fundamental frequency. High-pass filtering can be performed following normalisation of the PPG signals 42. The optical density ratio can be determined from the high-pass filtered red and infrared PPG signals, e.g. by using root mean squares (RMS): RMS (high-pass filtered red)/RMS (high-pass filtered infrared).

In some embodiments, information about the posture of the subject during the PPG signal measurement can be used in determining the $SpO_2$ measurement. Information about the posture of the subject can be derived from acceleration measurements from an accelerometer worn by the subject. Taking into account the posture of the subject during the PPG signal measurement can be used to increase the robustness of the determined $SpO_2$ measurement. For example, a PPG signal or part of a PPG signal can be excluded when determining $SpO_2$ if the subject is in a particular posture when that PPG signal or that part of the PPG signal was obtained. In some embodiments, for a chest-worn PPG sensor, the particular posture can be when the subject is lying on their side, as it has been found that PPG signals obtained when a subject is lying on their side results in deviations in $SpO_2$ measurements compared to other body postures. This may be due to poor contact of the PPG sensor with the skin, or due to folds of the skin.

It will be appreciated that the techniques described herein are not applicable solely to PPG signals obtained from PPG sensor(s) 6 positioned on the chest of the subject, and the techniques can be applied to PPG signals obtained from any body part of a subject. Furthermore, the techniques are not limited to use with PPG signals obtained using contact-based PPG sensors (i.e. transmissive or reflectance-based PPG sensors), and the techniques can also be applied to PPG signals obtained remotely using a camera.

Figure 6:
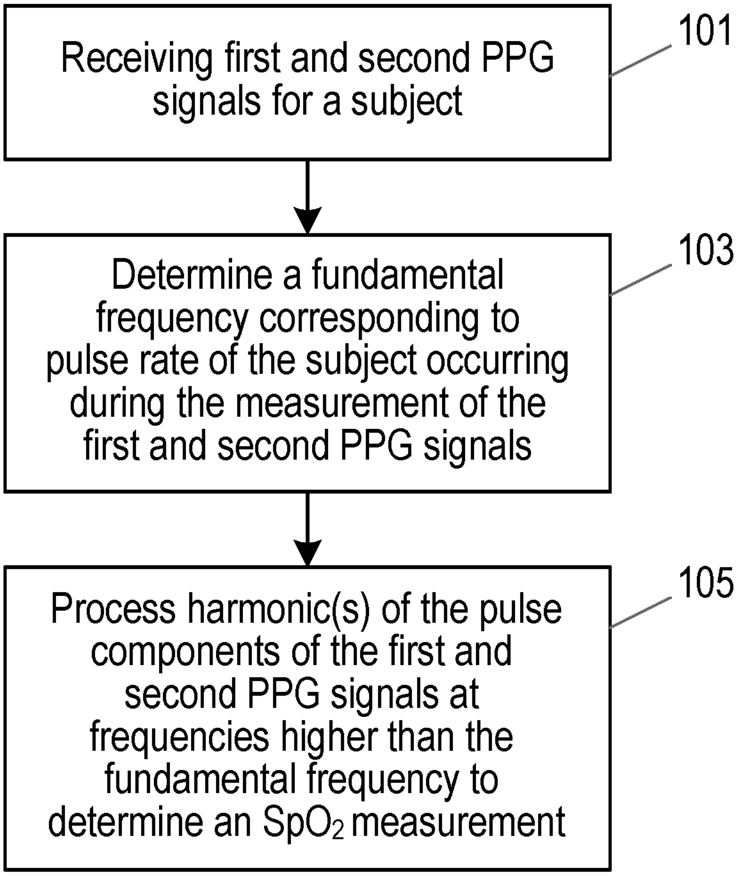
FIG. 6 is a flow chart illustrating a method of determining $SpO_2$ measurements according to an exemplary embodiment.

The flow chart in FIG. 6 illustrates a method for determining an $SpO_2$ measurement for a subject according to various embodiments. The method can be performed by the apparatus 4, for example by the processing unit 8. The processing unit 8 may perform the method as a result of executing suitably configured computer readable code.

In step 101, first and second PPG signals are received for the subject. The first PPG signal relates to, or includes measurements of, a first wavelength of light and the second PPG signal relates to, or includes measurements of, a second wavelength of light. In some embodiments, the first wavelength of light can be red light (e.g. with a wavelength of 660 nm) and the second wavelength of light can be infrared light (e.g. with a wavelength of 940 nm), or vice versa. The first and second PPG signals relate to the same time period. In some embodiments, multiple PPG signals can be received for each wavelength, for example from PPG sensors on different parts of the body of the subject, and these sets of first and second PPG signals processed according to the subsequent steps of the method.

The PPG sensor(s) 6 that generated the PPG signals may be contact-based PPG sensor(s) that obtain the PPG signal using a transmissive or reflectance-based measurement technique. Alternatively the PPG sensor(s) 6 that generated the PPG signals may be remote PPG sensor(s) (e.g. one or more cameras) that obtain the PPG signal without requiring direct contact with the skin of the subject.

In some embodiments, step 101 comprises receiving the PPG signals directly from PPG sensor(s) 6 as the PPG signals are generated. These embodiments enable the $SpO_2$ measurement to be determined in real time. In other embodiments, the PPG signals may be stored in the memory unit 10, and step 101 comprises retrieving the PPG signals from the memory unit 10.

The PPG signals include pulse components relating to the pulse/blood volume changes in the subject over time. The PPG signals can also include signal components due to noise and/or motion artefacts (including motion due to respiration). The pulse components of the PPG signal are a harmonic series in the PPG signal, with the pulse rate as the fundamental frequency (first harmonic) of the harmonic series. Thus, the pulse components include signal components at the pulse rate, and signal components at higher harmonics, i.e. at frequencies above the pulse rate.

Next, in step 103, the pulse rate of the subject occurring during the measurement of the first and second PPG signals is determined. The pulse rate is considered as a fundamental frequency (the first harmonic) in subsequent processing of the first and second PPG signals. Step 103 can comprise processing one or both of the first and second PPG signals to determine the pulse rate of the subject. Techniques for determining pulse rate from a PPG signal are known in the art, and will not be described further herein. In alternative embodiments, the pulse rate can be determined from measurements by a different sensor, such as an accelerometer, an ECG sensor, a BCG sensor, etc. In this case, the apparatus 4 or processing unit 8 can receive a signal from the different sensor (with the signal being measured at the same or similar time as the first and second PPG signals), and process the signal to determine the heart rate, which is indicative of the pulse rate.

Once the pulse rate has been determined in step 103, in step 105 the first and second PPG signals are processed to determine an $SpO_2$ measurement for the subject. In particular, one or more harmonics of the pulse components of the first and second PPG signals at frequencies higher than the fundamental frequency (the pulse rate) are processed to determine the $SpO_2$ measurement for the subject.

Step 105 can comprise determining the $SpO_2$ measurement from an optical density ratio derived from one or more harmonics of the pulse components of the first and second PPG signals that are higher than the fundamental frequency. That is, in step 105, the $SpO_2$ measurement is determined using harmonics of the pulse components of the first and second PPG signals at frequencies higher than the fundamental frequency—the pulse components of the PPG signals at, and below, the fundamental frequency are ignored or omitted in determining the $SpO_2$ measurement.

In some embodiments step 105 comprises processing the first PPG signal to determine the higher harmonics of the pulsatile component in the first PPG signal ($AC_1$) normalised by the non-pulsatile component of the first PPG signal ($DC_1$) and the higher harmonics of the pulsatile component in the second PPG signal ($AC_2$) normalised by the non-pulsatile component of the second PPG signal ($DC_2$). The $SpO_2$ measurement can be determined from the ratio of these normalised higher harmonic pulsatile components in line with Equation (1) above.

In alternative embodiments, step 105 can comprise determining the $SpO_2$ measurement from amplitudes of the higher harmonics of the pulse components of the first and second PPG signals at frequencies higher than the fundamental frequency.

Once the $SpO_2$ measurement has been determined, the $SpO_2$ measurement can be output by the apparatus 4. For example the $SpO_2$ measurement can be displayed to a user of the apparatus 4, e.g. the subject themselves, or a doctor or other care provider for the subject. In addition or alternatively, the $SpO_2$ measurement may be transmitted or otherwise provided to another device, such as a server or computer, that stores the $SpO_2$ measurements in a patient record for the subject.

In some embodiments, step 105 can comprise processing the higher harmonics of the first and second PPG signals in the time domain to determine the $SpO_2$ measurement. In other embodiments, step 105 can comprise processing the higher harmonics of the first and second PPG signals in the frequency domain to determine the $SpO_2$ measurement.

In some embodiments, step 105 can comprise applying a weighting to higher harmonics of the pulse components of the first and second PPG signals. The $SpO_2$ measurement is then determined from the weighted higher harmonics. Applying different weightings to the higher harmonics can increase or decrease the influence of a particular harmonic on the resulting $SpO_2$ measurement. In some embodiments, the weighting applied to respective higher harmonics of the pulse components can be based on one or more vital signs of the subject or other parameters, such as a respiration rate of the subject, a pulse rate of the subject, a position of a PPG sensor(s) 6 on the subject or relative to the subject, and measurements of movement and/or posture of the subject. In these embodiments, the apparatus 4 or system 2 may include one or more additional sensors for measuring these vital signs or parameters.

In some embodiments, for example those that use the APBV method to determine $SpO_2$, at least a third PPG signal is received in step 101 for a further wavelength of light, and processed in step 105 along with the first and second PPG signals to determine an $SpO_2$ measurement for the subject.

In alternative embodiments, step 105 can comprise selecting harmonics of the pulse components of the first and second PPG signals corresponding to one or more harmonics higher than the fundamental frequency. The $SpO_2$ measurement is then determined from the selected higher harmonics of the pulse components of the first and second PPG signals. In some embodiments, the selection of higher harmonics can be based on one or more vital signs of the subject or other parameters, such as a respiration rate of the subject, a pulse rate of the subject, a position of a PPG sensor(s) 6 on the subject or relative to the subject, and measurements of movement and/or posture of the subject. In these embodiments, the apparatus 4 or system 2 may include one or more additional sensors for measuring these vital signs or parameters.

In some embodiments, particularly where the PPG signals are processed in the time domain to determine the $SpO_2$ measurement, step 105 can comprise high-pass filtering the first and second PPG signals and processing the high-pass filtered PPG signals to determine the $SpO_2$ measurement. The cut-off frequency for the high-pass filter is above the fundamental frequency (the pulse rate). In some embodiments, the cut-off frequency may be above the lower harmonics of the pulse components (e.g. above the second harmonic, or above the third harmonic). In some embodiments, the value of the cut-off frequency can be set based on one or more vital signs of the subject or other parameters, such as a respiration rate of the subject, a pulse rate of the subject, a position of a PPG sensor(s) 6 on the subject or relative to the subject, and measurements of movement and/or posture of the subject. In these embodiments, the apparatus 4 or system 2 may include one or more additional sensors for measuring these vital signs or parameters.

Thus, there is provided a method and apparatus that provide measurements of $SpO_2$ of a subject that have improved reliability when compared to $SpO_2$ measurements determined using conventional techniques. In particular, the reliability of $SpO_2$ measurements determined using the techniques described herein from PPG signals obtained from the chest or other central body part can approach the reliability of $SpO_2$ measurements obtained from the fingertip using conventional processing techniques.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for determining an arterial blood oxygenation (SpO2) measurement for a subject, the method comprising:

receiving, in real time, a first and second photoplethysmogram, (PPG) signals for the subject, wherein the first PPG signal is obtained using a first wavelength of light and the second PPG signal is obtained using a second wavelength of light, wherein the first and second PPG signals comprise pulse components relating to blood volume changes in the subject over time;

determining a fundamental frequency corresponding to a pulse rate of the subject occurring during the measurement of the first and second PPG signals; and processing, repeatedly in real time, one or more higher harmonics of the pulse components of the first and second PPG signals at frequencies higher than the fundamental frequency to determine SpO2 measurements for the subject based on the processed one or more higher harmonics of the pulse components of the first and second PPG signals, excluding the fundamental frequency of the pulse components.

2. The method as claimed in claim 1, wherein the step of processing comprises:

applying respective weightings to the one or more higher harmonics; and processing the weighted higher harmonics to determine the SpO2 measurement.

3. The method as claimed in claim 1, wherein the step of processing comprises:

selecting one or more higher harmonics of the pulse components of the first and second PPG signals; and processing the selected one or more higher harmonics to determine the SpO2 measurement.

4. The method as claimed in claim 1, wherein the step of processing comprises:

high-pass filtering the first and second PPG signals with a cut-off frequency above the fundamental frequency; and processing the high-pass filtered first and second PPG signals to determine the SpO2 measurement.

5. The method as claimed in claim 2, wherein the respective weightings are based on one or more of a respiration rate of the subject, a pulse rate of the subject, a position of a PPG sensor on the subject or relative to the subject, and measurements of movement and/or posture of the subject.

6. The method as claimed in claim 1, wherein the step of processing one or more higher harmonics comprises:

determining the SpO2 measurement from an optical density ratio derived from the one or more higher harmonics of the first and second PPG signals.

7. The method as claimed in claim 1, wherein the step of processing one or more higher harmonics comprises:

determining the SpO2 measurement from amplitudes of the one or more higher harmonics.

8. An apparatus for determining an arterial blood oxygenation (SpO2) measurement for a subject, the apparatus comprising a processor configured to:

receive, in real time, first and second photoplethysmogram (PPG) signals for the subject, wherein the first PPG signal is obtained using a first set of wavelengths of light and the second PPG signal is obtained using a second set of wavelengths of light, wherein the first and second PPG signals comprise pulse components relating to blood volume changes in the subject over time;

determine a fundamental frequency corresponding to a pulse rate of the subject occurring during the measurement of the first and second PPG signals; and process, repeatedly in real time, one or more higher harmonics of the pulse components of the first and second PPG signals at frequencies higher than the fundamental frequency to determine SpO2 measurements for the subject based on the processed one or more higher harmonics of the pulse components of the first and second PPG signals, excluding the fundamental frequency of the pulse components.

9. The apparatus as claimed in claim 8, wherein the processor is configured to process the one or more higher harmonics by:

applying respective weightings to the one or more higher harmonics; and processing the weighted higher harmonics to determine the $SpO_2$ measurement.

10. The apparatus as claimed in claim 8, wherein the processor is configured to process the one or more higher harmonics by:

selecting one or more higher harmonics of the pulse components of the first and second PPG signals; and processing the selected one or more higher harmonics to determine the $SpO_2$ measurement.

11. The apparatus as claimed in claim 8, wherein the processor is configured to process the one or more higher harmonics by:

high-pass filtering the first and second PPG signals with a cut-off frequency above the fundamental frequency; and processing the high-pass filtered first and second PPG signals to determine the $SpO_2$ measurement.

12. The apparatus as claimed in claim 9, wherein the respective weightings are based on one or more of a respiration rate of the subject, a pulse rate of the subject, a position of a PPG sensor on the subject or relative to the subject, and measurements of movement and/or posture of the subject.

13. The apparatus as claimed in claim 8, wherein the processor is configured to process the one or more higher harmonics by:

determining the $SpO_2$ measurement from an optical density ratio derived from the one or more higher harmonics of the first and second PPG signals.

14. The apparatus as claimed in claim 8, wherein the processor is configured to process the one or more higher harmonics by:

determining the $SpO_2$ measurement from amplitudes of the one or more higher harmonics.

15. A tangible, non-transitory computer readable medium that stores executable instructions, which when executed by a processor, cause the processor to:

receive, in real time, first and second photoplethysmogram (PPG) signals for the subject, wherein the first PPG signal is obtained using a first set of wavelengths of light and the second PPG signal is obtained using a second set of wavelengths of light, wherein the first and second PPG signals comprise pulse components relating to blood volume changes in the subject over time;

determine a fundamental frequency corresponding to a pulse rate of the subject occurring during the measurement of the first and second PPG signals; and process, repeatedly in real time, one or more higher harmonics of the pulse components of the first and second PPG signals at frequencies higher than the fundamental frequency to determine SpO2 measurements for the subject based on the processed one or more higher harmonics of the pulse components of the first and second PPG signals, excluding the fundamental frequency of the pulse components.

16. The tangible, non-transitory computer readable medium of claim 15, wherein the instructions further cause the processor to process the one or more higher harmonics by:

applying respective weightings to the one or more higher harmonics; and processing the weighted higher harmonics to determine the $SpO_2$ measurement.

17. The tangible, non-transitory computer readable medium of claim 15, wherein the instructions further cause the processor to process the one or more higher harmonics by:

selecting one or more higher harmonics of the pulse components of the first and second PPG signals; and processing the selected one or more higher harmonics to determine the $SpO_2$ measurement.

18. The tangible, non-transitory computer readable medium of claim 15, wherein the instructions further cause the processor to process the one or more higher harmonics by:

high-pass filtering the first and second PPG signals with a cut-off frequency above the fundamental frequency; and processing the high-pass filtered first and second PPG signals to determine the $SpO_2$ measurement.

19. The tangible, non-transitory computer readable medium of claim 16, wherein the respective weightings are based on one or more of a respiration rate of the subject, a pulse rate of the subject, a position of a PPG sensor on the subject or relative to the subject, and measurements of movement and/or posture of the subject.

20. The tangible, non-transitory computer readable medium of claim 15, wherein the instructions further cause the processor to process the one or more higher harmonics by:

determining the $SpO_2$ measurement from an optical density ratio derived from the one or more higher harmonics of the first and second PPG signals.

* * * * *